United States Patent
Brand et al.

(10) Patent No.: US 9,675,765 B2
(45) Date of Patent: Jun. 13, 2017

(54) SAFETY DEVICE FOR A LIQUID INJECTION SYRINGE, AND A SYRINGE ASSEMBLY INCLUDING THE DEVICE

(75) Inventors: Julien Brand, Saint Clair de la Tour (FR); Pascal Dugand, Estrablin (FR); Sylvain Lanzi, Chirens (FR); Thierry Rimlinger, L'isle d'Abreau (FR)

(73) Assignee: REXAM PHARMA LA VERPILLIERE, La Verpilliere (FR)

( * ) Notice: Subject to any disclaimer, the term of this patent is extended or adjusted under 35 U.S.C. 154(b) by 1083 days.

(21) Appl. No.: 12/285,770

(22) Filed: Oct. 14, 2008

(65) Prior Publication Data

US 2009/0105663 A1    Apr. 23, 2009

Related U.S. Application Data

(60) Provisional application No. 60/960,978, filed on Oct. 23, 2007.

(30) Foreign Application Priority Data

Oct. 11, 2007    (FR) ...................... 07 58231

(51) Int. Cl.
  *A61M 5/34*    (2006.01)
  *A61M 5/32*    (2006.01)
  *A61M 5/31*    (2006.01)

(52) U.S. Cl.
  CPC ............ *A61M 5/344* (2013.01); *A61M 5/326* (2013.01); *A61M 5/3129* (2013.01);
  (Continued)

(58) Field of Classification Search
  CPC ........ A61M 2005/3247; A61M 5/3243; A61M 5/322; A61M 2005/3217;
  (Continued)

(56) References Cited

U.S. PATENT DOCUMENTS 2,453,590 A * 11/1948 Poux .............................. 604/201
4,425,120 A *  1/1984 Sampson ............ A61M 5/3271
                                          604/198

(Continued)

FOREIGN PATENT DOCUMENTS

FR         2 830 765 A1    4/2003
WO    WO 03/047664 A1     6/2003
  (Continued)

*Primary Examiner* — Bradley Osinski
*Assistant Examiner* — Matthew A Engel
(74) *Attorney, Agent, or Firm* — Oliff PLC

(57) ABSTRACT

The syringe comprises a body containing the liquid and having fitted thereto an endpiece for fastening a needle carrier. The safety device comprises a protective sheath and a syringe support that is received inside the sheath. The sheath and the support are axially movable relative to each other between two positions, namely an uncovered position of the needle, and a retracted position of said needle. The support includes anti-rotation means for constraining it in rotation about its axis and comprising at least one pawl urged resiliently into a position in which the pawl is designed to co-operate with complementary anti-rotation means of the fastener endpiece. The sheath and the support include complementary anti-rotation means for constraining them in rotation relative to each other about their axes and activated at least when the sheath and the support are in their uncovered position of the needle.

15 Claims, 6 Drawing Sheets

(52) U.S. Cl.
CPC ......... *A61M 5/3202* (2013.01); *A61M 5/3271* (2013.01); *A61M 5/347* (2013.01); *A61M 2005/3104* (2013.01); *A61M 2005/3247* (2013.01); *A61M 2005/3261* (2013.01); *A61M 2005/3264* (2013.01)

(58) Field of Classification Search
CPC .... A61M 2005/2073; A61M 2005/202; A61M 5/326; A61M 5/344
USPC .................................. 604/110, 192–198, 263
See application file for complete search history.

(56) References Cited

U.S. PATENT DOCUMENTS

| | | | | |
|---|---|---|---|---|
| 4,695,274 A * | 9/1987 | Fox | A61M 5/3271 | 604/198 |
| 4,702,738 A * | 10/1987 | Spencer | A61M 5/3272 | 604/198 |
| 4,737,144 A * | 4/1988 | Choksi | A61M 5/3243 | 604/198 |
| 4,813,426 A * | 3/1989 | Haber | A61B 5/1438 | 600/576 |
| 4,840,185 A * | 6/1989 | Hernandez | A61B 5/1438 | 600/576 |
| 4,874,383 A * | 10/1989 | McNaughton | A61M 5/3271 | 604/198 |
| 4,900,310 A * | 2/1990 | Ogle, II | A61B 5/1444 | 604/198 |
| 4,915,702 A * | 4/1990 | Haber | A61B 5/1438 | 600/576 |
| 4,923,446 A * | 5/1990 | Page et al. | A61M 5/3243 | 604/198 |
| 4,950,241 A * | 8/1990 | Ranford | A61M 5/322 | 604/110 |
| 4,994,045 A * | 2/1991 | Ranford | A61M 5/3271 | 604/198 |
| 4,998,924 A * | 3/1991 | Ranford | A61M 5/3271 | 604/110 |
| 5,019,051 A * | 5/1991 | Hake | A61M 5/3271 | 604/197 |
| 5,024,660 A * | 6/1991 | McNaughton | A61M 5/3271 | 604/110 |
| 5,088,988 A * | 2/1992 | Talonn | A61M 5/3271 | 604/198 |
| 5,127,910 A * | 7/1992 | Talonn | A61M 5/3271 | 604/110 |
| 5,147,326 A * | 9/1992 | Talonn | A61M 5/3202 | 604/110 |
| 5,156,599 A * | 10/1992 | Ranford | A61M 5/3271 | 128/919 |
| 5,217,437 A * | 6/1993 | Talonn | A61M 5/3271 | 600/576 |
| 5,267,977 A * | 12/1993 | Feeney, Jr. | A61M 5/3271 | 604/198 |
| 5,338,311 A * | 8/1994 | Mahurkar | A61B 5/1405 | 604/110 |
| 5,415,645 A * | 5/1995 | Friend et al. | | 604/110 |
| 5,417,660 A * | 5/1995 | Martin | | 604/110 |
| 5,611,785 A * | 3/1997 | Mito | A61M 5/288 | 604/239 |
| 6,162,197 A * | 12/2000 | Mohammad | A61B 5/1438 | 604/195 |
| 6,572,565 B2 * | 6/2003 | Daley | A61B 5/1438 | 600/573 |
| 6,752,783 B2 * | 6/2004 | Hung et al. | | 604/110 |
| 7,390,312 B2 * | 6/2008 | Barrelle | | 604/110 |
| 2001/0005781 A1 * | 6/2001 | Bergens et al. | | 604/208 |
| 2003/0069518 A1 * | 4/2003 | Daley | A61B 5/1438 | 600/576 |
| 2004/0127857 A1 | 7/2004 | Shemesh et al. | | |
| 2005/0165353 A1 | 7/2005 | Pessin | | |
| 2006/0036216 A1 * | 2/2006 | Rimlinger et al. | | 604/198 |
| 2006/0095010 A1 * | 5/2006 | Westbye | | 604/197 |
| 2009/0105663 A1 * | 4/2009 | Brand et al. | | 604/197 |

FOREIGN PATENT DOCUMENTS

| | | |
|---|---|---|
| WO | WO 03/077977 A2 | 9/2003 |
| WO | WO 2005/089831 A1 | 9/2005 |
| WO | WO 2006/050304 A1 | 5/2006 |
| WO | WO 2007/109352 A2 | 9/2007 |

\* cited by examiner

SAFETY DEVICE FOR A LIQUID INJECTION SYRINGE, AND A SYRINGE ASSEMBLY INCLUDING THE DEVICE

FIELD OF THE INVENTION

The present invention relates to the field of a safety device for a liquid injection syringe, in particular for a prefilled syringe.

BACKGROUND OF THE INVENTION

In the prior art, and in particular from WO 2006/050304, a liquid injection syringe is known of the type that comprises a body of generally tubular shape forming a reservoir for the liquid and having fitted thereto an endpiece of generally annular shape for fastening a needle carrier on the syringe body.

The fastener endpiece is sometimes referred to as a "luer lock" and the needle carrier is sometimes referred to as a "luer needle".

The syringe also includes a plunger mounted to be movable axially in the body between a ready position and an end-of-liquid-injection position.

Below, an element is said to be "proximal" or "distal" depending on whether it is axially close to or far away from the end of the plunger that is to be actuated by a user.

WO 2006/050304 also describes a safety device for a syringe of the above-specified type, the safety device being of the type comprising:
  a first member of generally tubular shape, referred to below as a protective sheath; and
  a second member of generally tubular shape, referred to below as a syringe support, which second member is received in the sheath, substantially coaxially therewith.

The protective sheath and the syringe support are movable axially relative to each other between two positions, referred to below as the uncovered position of the syringe needle and the retracted position of said needle.

The safety device enables the needle to be retracted automatically into the sheath so as to ensure that a person handling the syringe assembly after it has been used normally, i.e. after the liquid has been injected into the body of a patient, cannot accidentally be pricked by the needle.

The fastener endpiece includes a proximal end that is generally engaged on a distal end of the syringe body that is generally conical in shape.

Furthermore, the fastener endpiece includes a distal end designed to co-operate with a needle carrier by screw fastening. The needle carrier and the needle it carries are generally covered prior to use of the syringe by a cap. Where appropriate, prior to putting the needle carrier into position on the syringe body, a plug for closing the syringe body is screwed onto the fastener endpiece.

The torque needed for unscrewing the plug or for screwing on the needle carrier can cause the fastener endpiece to turn about the axis of the syringe body. It is therefore necessary to be able to oppose turning of the fastener endpiece, particularly in order to be able to unscrew the plug or to screw on the needle carrier.

Unfortunately, after the syringe has been mounted in the safety device, the fastener endpiece is generally rendered practically inaccessible by the protective endpiece that covers it. The user therefore cannot act directly on the fastener endpiece to prevent it from turning, in particular while unscrewing the plug or screwing on the needle carrier.

WO 2006/050304 proposes means for preventing the fastener endpiece from turning, which means comprise in particular a pair of tongues provided in the protective sheath and in the syringe support. When the syringe and the support are in their relative uncovered position of the syringe needle, the tongue of the sheath covers the tongue of the syringe support. The tongues are elastically deformable in a radial direction. To prevent the fastener endpiece from turning, the user presses on the tongue of the sheath so as to push it radially towards the axis of the sheath, thereby pushing the tongue of the support (which is covered by the tongue of the sheath) until it comes into contact with the fastener endpiece.

OBJECT AND SUMMARY OF THE INVENTION

An object of the invention is to provide means for preventing the fastener endpiece from turning, which means are simpler to those described in WO 2006/050304, said turn-preventing means being suitable for being activated without the user being required to perform any special action in order to prevent such turning.

To this end, the invention provides a safety device for a liquid injection syringe comprising a body of generally tubular shape forming a reservoir for the liquid and having fitted thereon an endpiece of generally annular shape for fastening a needle carrier on the syringe body, the device being of the type comprising:
  a first member of generally tubular shape, referred to as a protective sheath; and
  a second member of generally tubular shape, referred to a syringe support, received inside the sheath, substantially coaxially therewith;
  the sheath and the support being movable axially relative to each other between two positions, namely an uncovered position of the syringe needle, and a retracted position of said needle;
  wherein:
  the syringe support includes first anti-rotation means for constraining rotation about its axis and comprising at least one pawl urged resiliently into a position in which the pawl is designed to co-operate with complementary anti-rotation means carried by the fastener endpiece; and
  the protective sheath and the syringe support include second complementary anti-rotation means for constraining them in rotation relative to each other about their axes, these second anti-rotation means being activated at least when the sheath and the support are in their relative uncovered position of the needle.

The first anti-rotation means are simple and effective.

Indeed, assume that a closure plug for the syringe is screwed onto the fastener endpiece. By means of the pawl, the fastener endpiece is prevented from rotating relative to the syringe support, either even before a user begins to unscrew the plug, or else after the plug has started to be unscrewed over a short stroke. Furthermore, since the second complementary anti-rotation means constrain the syringe support in rotation with the sheath, the fastener endpiece is consequently, by transitivity, prevented from turning relative to the sheath. Thus, a user taking hold of the sheath can easily unscrew the plug carried by the fastener endpiece and then screw a needle carrier onto said fastener endpiece, without those screwing and unscrewing operations being impeded by unwanted turning of the fastener endpiece.

A safety device of the invention may also include at least one of the following optional characteristics:

the syringe support carries at least two diametrically-opposite anti-rotation pawls;

the pawl is formed by an axial tab molded integrally with the syringe support and urged resiliently radially towards the axis of said syringe support, being designed to co-operate with a complementary anti-rotation groove formed in the outline of the fastener endpiece;

the sheath includes at least one radial setback that is positioned, when the sheath and the support are in their relative uncovered position of the syringe needle, to be radially aligned with the anti-rotation axial tab so as to allow said tab to move radially against its return force;

the axial anti-rotation tab is carried by a distal end of the syringe support, and the radial setback is formed by an axial slot provided in a distal end of the sheath;

the second complementary anti-rotation means comprise at least one complementary pair constituted by a projection and a groove provided on or in the syringe support and the protective sheath;

the projection of the second anti-rotation means is provided on a proximal end of the syringe support, and the groove of the second anti-rotation means is formed by a slot provided in a proximal end of the protective sheath;

the second complementary anti-rotation means comprise two diametrically-opposite complementary pairs, each comprising a projection and a groove; and the device includes third complementary anti-rotation means for constraining the support and the sheath in rotation relative to each other about their axes, these third means being activated at least during axial displacement of the sheath and the support relative to each other from the uncovered position of the syringe needle towards the retracted position of said needle. These third means serve in particular to prevent the support from turning relative to the sheath while a spring is relaxing.

The invention also provides a syringe assembly of the type comprising:

a liquid injection syringe comprising a body of generally tubular shape forming a reservoir for the liquid and having fitted thereon an endpiece of generally annular shape for fastening a needle carrier to the syringe body; and a safety device for the syringe;

wherein the safety device is as defined above.

An assembly of the invention may also include at least one of the following optional characteristics:

the outline of the fastener endpiece is of generally crenellated shape defining a plurality of angularly distributed anti-rotation axial grooves; and the fastener endpiece is designed to co-operate by screw-fastening with a plug for closing the syringe or the needle carrier.

BRIEF DESCRIPTION OF THE DRAWINGS

The invention can be better understood on reading the following description given purely by way of example and made with reference to the drawings, in which.

MORE DETAILED DESCRIPTION

Figure 1:
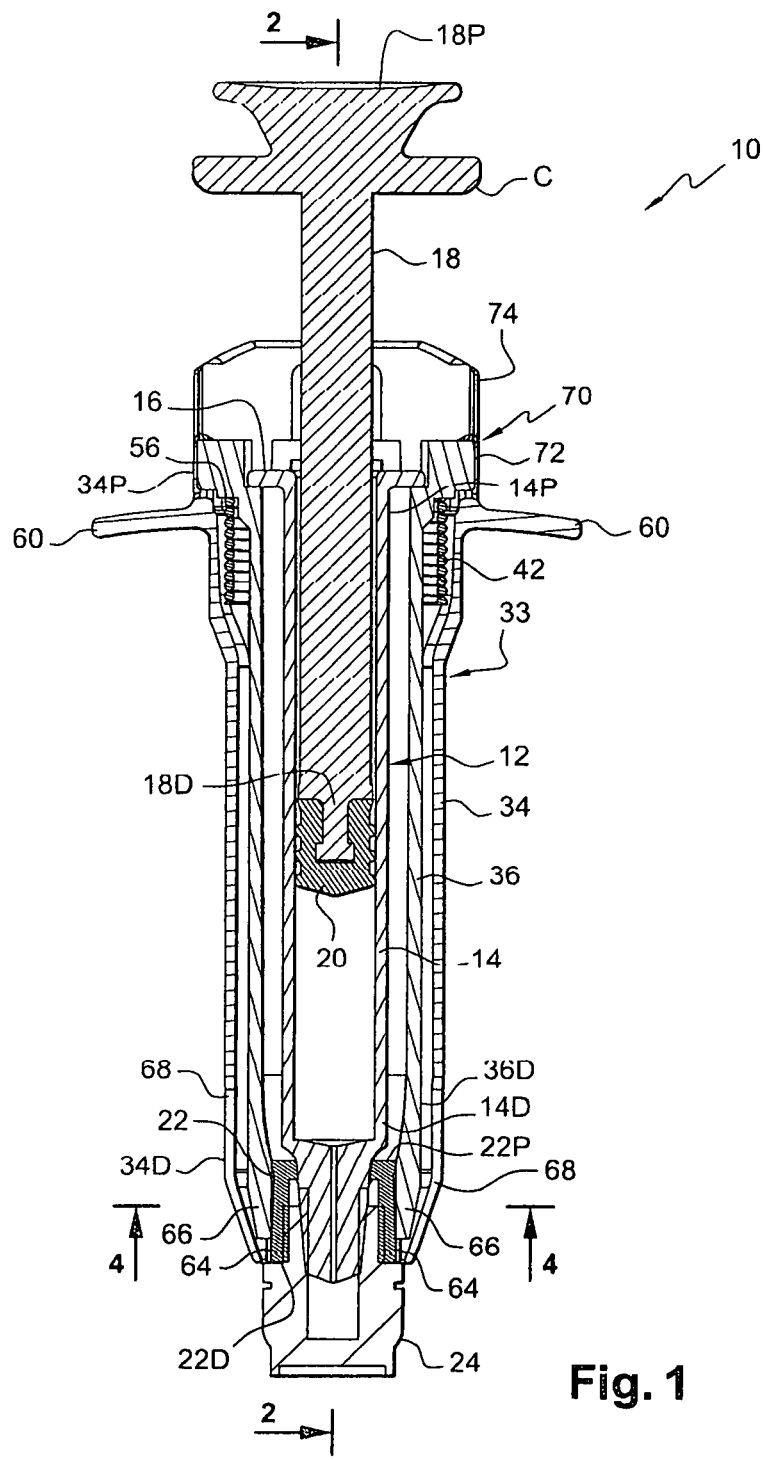
FIG. 1 is an axial section view of a syringe assembly of the invention, the syringe being provided with a fastener endpiece on which there is screwed a syringe closure plug for plugging the syringe.
Figure 2:
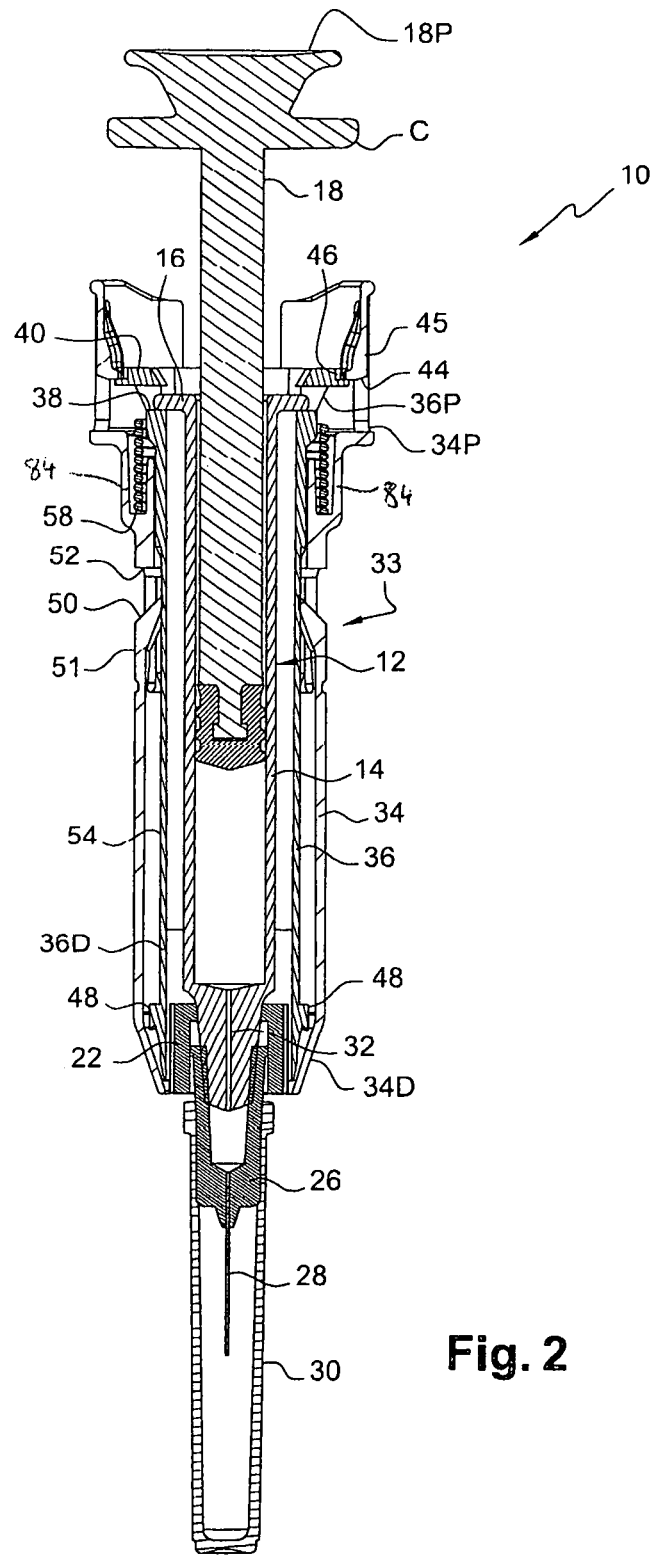
FIG. 2 is a section view on line 2-2 of FIG. 1, in which the plug has been replaced by a needle carrier screwed onto the fastener endpiece, the assembly being in a configuration prior to the syringe being used.
Figure 3:
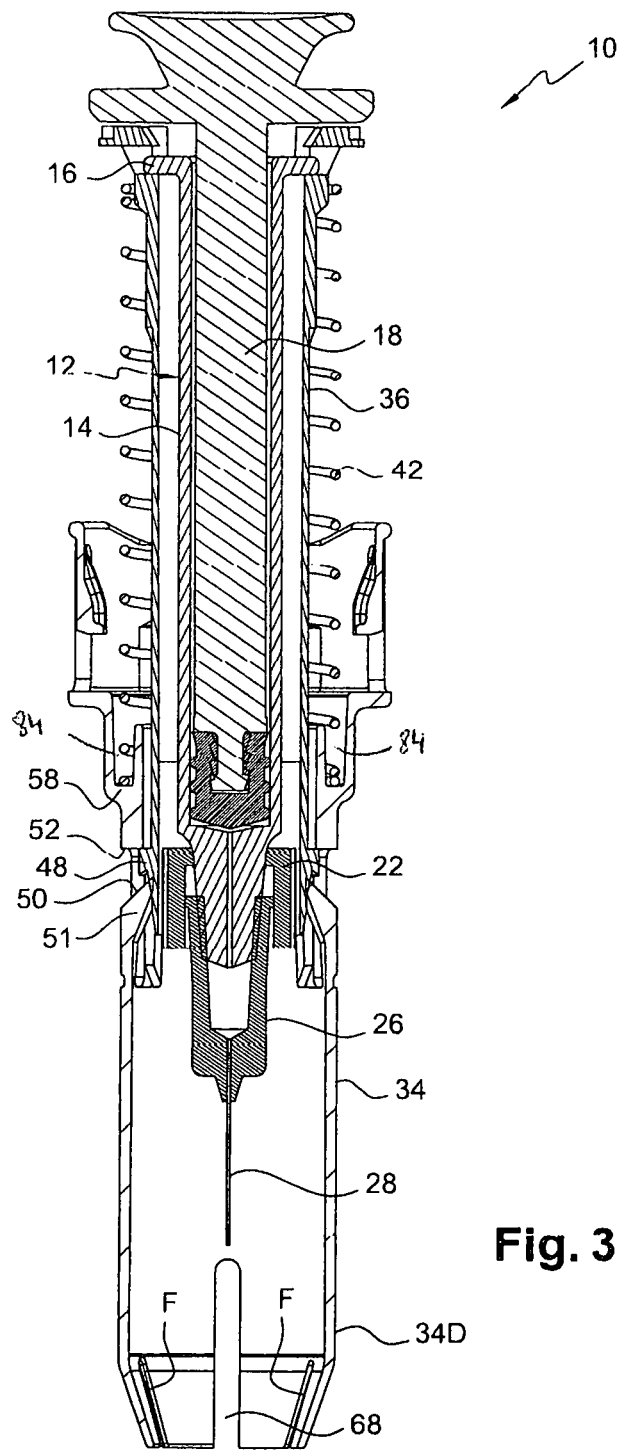
FIG. 3 is a view similar to FIG. 2, the assembly being in a configuration after the syringe has been used.

FIGS. 1 to 3 show a syringe assembly of the invention, given overall reference 10.

The assembly 10 comprises a conventional syringe 12 for injecting a liquid, in particular a medical liquid.

The syringe 12 has a tubular syringe body 14 forming a reservoir for the liquid. The body 14 has an open proximal end 14P provided with a collar 16, and a distal end 14D that is generally in the form of a cone converging away from the proximal end 14P.

The syringe 12 also includes a plunger 18 mounted to move axially in the body 14 between a ready position as shown in FIGS. 1 and 2 and a position at the end of injecting liquid, as shown in FIG. 3.

The plunger 18, e.g. made of plastics material, has a proximal end 18P outside the body 14, and a distal end 18D inside the body 14 and carrying a conventional piston 20. The proximal end 18P of the plunger forms a plunger drive end.

The syringe 12 also has an endpiece 22 for fastening a syringe closure plug 24, as shown in FIG. 1, or a needle carrier 26 as shown in FIGS. 2 and 3.

The fastener endpiece 22 of generally annular shape has a proximal end 22P engaged in known manner against a complementary surface of the distal end 14D of the body 14. The fastener endpiece 22 also has a distal end 22D provided with a threaded inside surface for screw co-operation with a complementary threaded surface of the closure plug 24 or of the needle carrier 26.

The needle carrier 26 carries a needle 28 suitable for being protected by a removable cap 30 that is engaged on the needle carrier 26, as shown in FIG. 2.

An axial channel 32 formed in the distal end 14D of the syringe body 14 enables liquid to pass between the body 14 and the needle carrier 26.

The assembly 10 also has a safety device 33 of the invention.

The device 33 comprises a first member of generally tubular shape, referred to as a protective sheath 34, and a second member of generally tubular shape, referenced to as a syringe support 36. The support 36 is housed inside the sheath 34, being substantially coaxial therewith.

The sheath 34 and the support 36 are made of plastics material, for example.

The sheath 34 and the support 36 are movable axially relative to each other between a first position, referred to as a disengaged position of the needle, as shown in FIGS. 1 and 2, and a second position, referred to as a retracted position of the needle, as shown in FIG. 3. The retracted position of the needle includes a covered position of the needle such that the sheath 34 at least partly covers the needle, as shown, for example, in FIG. 3.

The body 14 of the syringe is housed in a known manner in the support 36. More particularly, the syringe body 14 is prevented from moving axially (possibly with clearance) in the syringe support 36 by the collar 16 snap-fastening between a bearing seat 38 formed in the support 36 and at least one retractable locking abutment 40 secured to the support 36 (see FIG. 2, in particular). In the example described, the support 36 has two diametrically-opposite locking abutments 40.

Where appropriate, the radial and transverse clearances between the collar 16 and the housing formed by the seat 38 and the abutments 40 can be limited by co-operation between complementary shapes.

Figure 7:
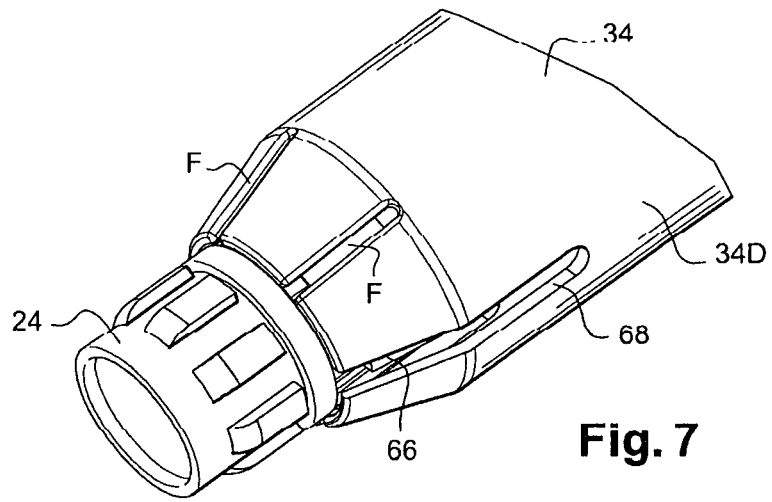
FIG. 7 is a view similar to FIG. 6 showing in addition, compared with FIG. 6, the protective sheath covering the syringe support.

It should be observed that the protective sheath 34 is provided with a distal end 34D of generally converging shape going away from the proximal end 34P of the sheath (see in particular FIG. 7). This distal end 34D is provided with axial slots or openings F enabling said distal end 34D to deform elastically, in particular to enable the diameter of the opening out at the distal end 34D to vary elastically, thereby allowing elements of various diameters making up the assembly 10 to pass through this opening.

Furthermore, the safety device 33 includes means for retaining the support 36 in the needle uncovered position relative to the sheath 34. These retaining means oppose the resilient force of return means comprising a thrust spring 42. As shown in FIG. 2, it can be seen that in the needle uncovered position, the spring 42 is housed in a groove 84 of generally annular shape, formed in this example in the proximal end 34P of the sheath 34. This groove 84 also serves to position the spring 42 both axially and radially.

With reference to FIG. 2, it can be seen that in the example shown the retaining means comprise at least one pair of complementary retaining abutments 44 and 46. A first retaining abutment 44 is formed by the free end of an axial tongue 45 provided in a proximal end 34P of the sheath 34. This tongue 45 is elastically deformable in a radial direction. The second retaining abutment 46 is formed on a proximal end 36P of the syringe support 36. The safety device 33 preferably has two pairs of diametrically-opposite retaining abutments 44 and 46.

The safety device 33 also has locking means for locking the sheath 34 in the retracted position of the needle 28, as shown in FIG. 3.

With reference to FIGS. 2 and 3, it can be seen in the example shown that the locking means comprise at least one radial projection 48 formed in a distal end 36D of the syringe support 36 for snap-fastening between a pair of abutments 50, 52 for preventing axial movement. A first abutment 50 for preventing axial movement is formed by the free end of an axial tongue 51 in the sheath 34. This tongue 51 is elastically deformable in a radial direction. The second abutment 52 for preventing axial movement is likewise in the sheath 34.

Preferably, the safety device 33 has a diametrically-opposite pair of radial projections 48, each projection 48 serving to co-operate with a pair of abutments 50 and 52 for preventing axial movement.

Figure 5:
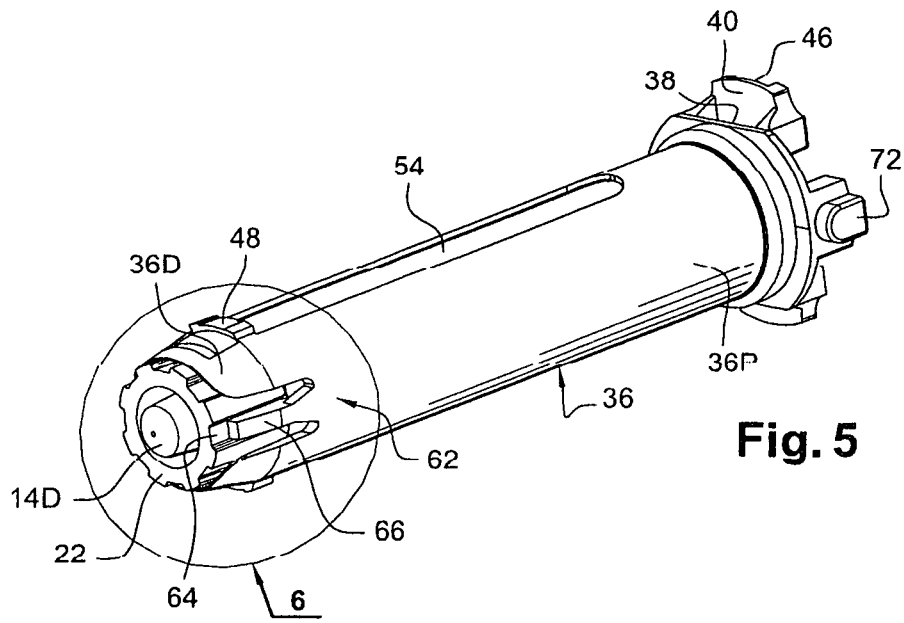
FIG. 5 is a perspective view of a portion of the syringe assembly shown in FIGS. 1 to 3, and in particular including the syringe support and the fastener endpiece of the needle carrier.

It should be observed that each abutment 50 for preventing axial movement contributes to guiding the syringe support 36 axially relative to the sheath 34 in co-operation with an axial groove 54 formed in the support 36 and clearly visible in FIG. 5.

The spring 42 bears firstly against an outer, first seat 56 formed on the syringe support 36 (see FIG. 1), and secondly on an inner, second seat 58 formed in the sheath 34 (see FIG. 2). This inner, second seat 58 is formed by the bottom of the groove 84 housing the spring 42 in the uncovered position of the needle 28.

The sheath 34 has external grip means designed to be gripped by the fingers of a user for injecting liquid by axially moving the drive end 18P of the plunger towards said grip means.

In the example described, the grip means comprise two outer radial tabs 60 secured to the sheath 34 (see FIG. 1).

The safety device 33 is assembled and then the syringe 12 is assembled in the safety device 33 in known manner, e.g. as proposed in FR-A-2 830 765.

Furthermore, with the exception of certain aspects associated with the invention, and that are described in greater detail below, the operation of the safety device 33 is conventional, e.g. like that described in FR-A-2 830 765.

The principal stages in the operation of the safety device 33 are outlined below with reference to FIGS. 2 and 3.

Prior to use, the assembly 10 is in a ready configuration as shown in FIG. 2. The cap 30 for protecting the needle 28 is engaged on the needle carrier 26. The sheath 34 and the support 36 are held in their relative uncovered position of the needle 28 by co-operation between the complementary retaining abutments 44 and 46.

Initially, the user removes the cap 30 so as to disengage needle 28.

In order to inject the liquid, the user takes hold of the assembly 10 so as to push the plunger 18 into the syringe body 12 by moving the proximal end 18P of the plunger axially towards the grip tabs 60.

The user pushes in the plunger 18 until the end-of-injection position as shown in FIG. 3 is reached.

While the plunger 18 is being pushed in, the proximal end 18P of the plunger, which presents a suitable outline C, co-operates with the resilient tongues 45 so as to separate the complementary retaining abutments 44 and 46 from each other. When these retaining means are released, the spring 42 urges the syringe support 36 so as to place the sheath 34 and the support 36 into their relative position in which the needle 28 is retracted, as shown in FIG. 3.

When the assembly 10 is in the configuration shown in FIG. 3, the radial projections 48 are snapped between the axial abutments 50 and 52 for preventing radial movement so as to lock the sheath 34 and the support 36 in their retracted position of the needle 28.

In accordance with the invention, the fastener endpiece 22 and the syringe support 36 include complementary anti-rotation means 62 for constraining them in rotation about their axes.

Figure 4:
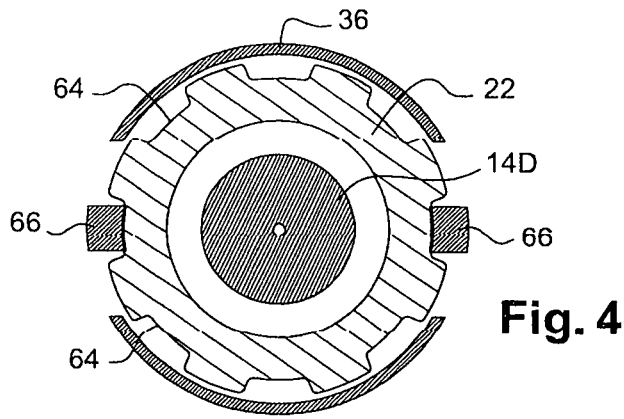
FIG. 4 is a section on a larger scale on line 4-4 of FIG. 1.
Figure 6:
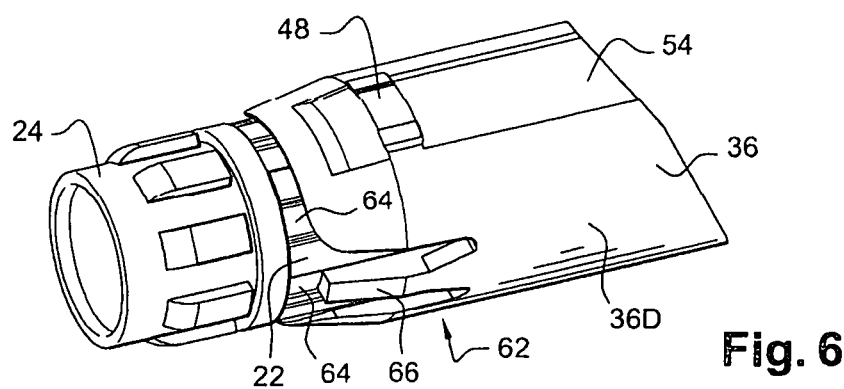
FIG. 6 is a detail view of the circled portion 6 of FIG. 5 showing, in addition to FIG. 5, a plug for the syringe screwed onto the fastener endpiece.

By way of example, the anti-rotation means 62 comprise firstly an outline of the fastener endpiece 22 having a generally crenellated shape defining a plurality of axial grooves 64 for providing constraint in rotation that are distributed angularly (see in particular FIGS. 4 to 6).

Secondly, the anti-rotation means 62 comprise two pawls 66 or latches for providing constraint in rotation that are carried by the syringe support 36. These pawls 66 are diametrically opposite.

With reference in particular to FIGS. 5 and 6, it can be seen in the example described that each pawl 66 is formed by an axial tab made integrally with the distal end 36D of the syringe support and that is elastically deformable in a radial direction. This tab forming the pawl 66 is resiliently urged radially towards the axis of the syringe support 36, towards a position in which it co-operates with a complementary axial groove 64 for providing constraint in rotation. Thus, each pawl 66 is urged resiliently into a position in which the pawl 66 co-operates with a groove 64 forming anti-rotation means carried by the fastener endpiece 22.

In a variant, the syringe support 36 need only have one pawl 66 or it could have more than two, for co-operating with complementary anti-rotation means carried by the fastener endpiece 22.

Figure 8:
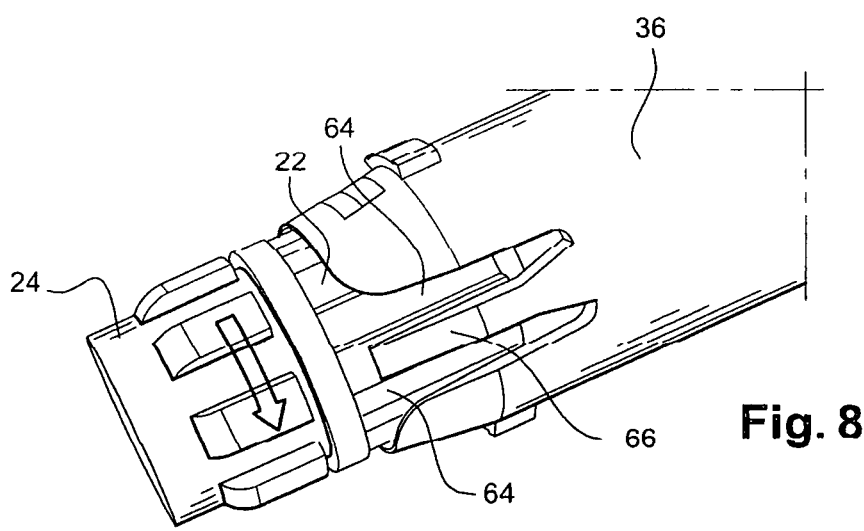
FIG. 8 is a view similar to FIG. 6 showing the fastener endpiece in an angular position relative to the syringe support that is different from the position shown in FIG. 6.

Preferably, the sheath 34 includes a radial setback 68 (see in particular FIGS. 1 and 7) such that when the sheath 34 and the support 36 are in their relative position in which the needle 38 is uncovered, as shown in FIGS. 1 and 2, the setback is radially aligned with the pawl-forming tab 66. This setback 68 allows the pawl-forming tab 66 to move radially against its return force. The pawl-forming tab 66 is moved against its return force, in particular when it bears against a portion of the outline of the fastener endpiece 22 between two of the grooves 64, as shown in FIG. 8.

The radial setback 68 is preferably in the form of an axial groove or slot formed in the distal end 34D of the sheath.

The sheath 34 and the support 36 include complementary anti-rotation means 70 for constraining them together in rotation about their axes. These anti-rotation means 70 are active at least when the sheath 34 and the support 34 are in their relative position in which the needle 28 is uncovered, as shown in FIGS. 1 and 2.

The means 70 also provide means for axially retaining the syringe body 14 relative to the sheath 34 during injection of the liquid.

With reference in particular to FIGS. 1 and 5, it can be seen in the example shown that the complementary anti-rotation means 70 comprise two complementary pairs, each pair being constituted by a radial projection 72 and an axial groove 74 formed on the support 36 and the sheath 34.

The two complementary pairs, each constituted by a radial projection 72 and an axial groove 74, are diametrically opposite.

In a variant, the safety device 33 need only have one pair constituted by a radial projection 72 and an axial groove 74.

In another variant, the anti-rotation means 70 could comprise an axial projection formed on the support 36 co-operating with a complementary shape provided in the sheath 34, or indeed complementary flats formed on the support 36 and the sheath 34.

The radial projection 72 is preferably provided at the proximal end 36P of the syringe support. The complementary axial groove 74 is formed by an axial slot formed in the proximal end 34P of the sheath.

The anti-rotation means 62 and 70 serve to prevent the fastener endpiece 22 from turning relative to the sheath 34. When mounting the syringe 12 in the safety device 33, the plug 24 is generally screwed onto the fastener endpiece 22. Two circumstances can then arise.

In a first circumstance, the relative angular position of the fastener endpiece 22 and of the syringe support 36 during assembly is such that the pawls 66 snap into the corresponding groove 64, automatically under the effect of the resilient return force of the pawls 66, as shown in FIGS. 4 to 7. The fastener endpiece 22 is then constrained in rotation relative to the syringe body 36. Furthermore, since the sheath 34 and the support 36 are in their relative position in which the needle is uncovered, they are constrained relative to each other in rotation by the means 72. The fastener endpiece 22 is thus correspondingly constrained in rotation relative to the protective sheath 36. Thus, a user taking hold of the sheath 34 can easily unscrew the plug 24 carried by the fastener endpiece 22 and then screw the needle carrier 26 onto said fastener endpiece 22 in order to obtain an assembly 10 in a configuration of the kind shown in FIG. 2. These screwing and unscrewing operations are easily performed since under normal conditions of use there is no unwanted rotation of the fastener endpiece 22 relative to the syringe body 14.

In the second circumstance, after the syringe 12 has been mounted in the safety device 33, each pawl 66 slides between two grooves 64, as shown in FIG. 8. It then suffices to turn the fastener endpiece 22 by a small amount, e.g. by using the plug 24 (which includes grip means) so as to cause the pawls 66 to snap into corresponding grooves 64, thereby returning to the first circumstance described above.

Figure 9:
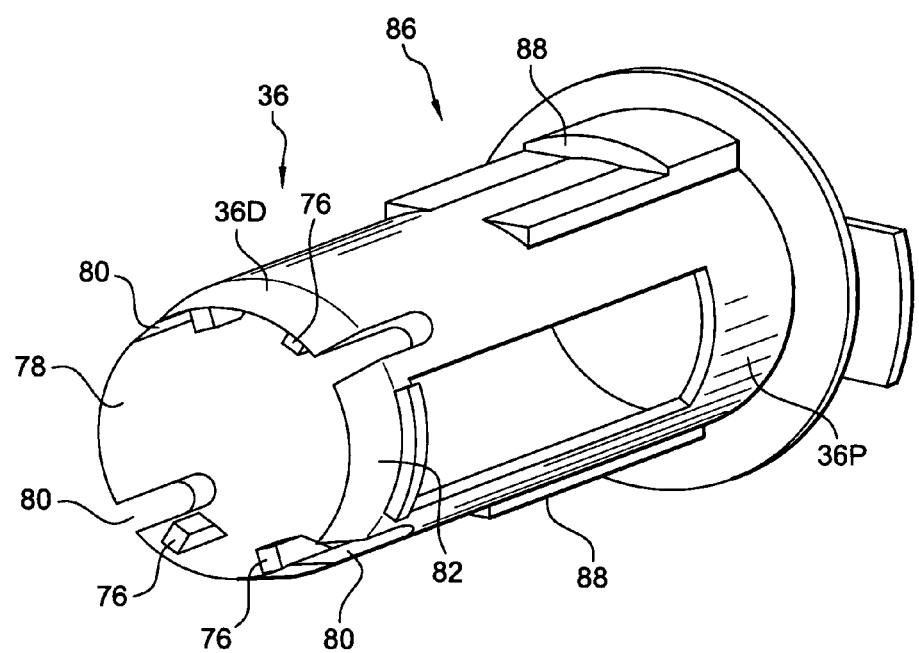
FIG. 9 is a perspective view of the syringe support of the syringe assembly shown in FIGS. 1 to 3, in two variants of the invention.

In a first variant of the invention as shown in FIG. 9, the syringe support 36 carries at least one pawl 76 formed by an axial projection formed of an inside surface 78 of the distal end 36D of the support 36. As shown in FIG. 9, in this variant the distal end 36D of the support 36 is provided with axial slots 80 enabling the distal end 36D to deform elastically in a radial direction. In this example, the distal end 36D has four axial slots 80 defining four substantially equal portions 82, and the support 36 carries two pairs of pawls 76 that are distributed on two diametrically-opposite portions 82.

Because the distal end 36D is elastically deformable in a radial direction, it is possible to vary the diameter of said end 36D elastically. Thus, each pawl 76 carried by the portions 82 of said end 36D can be urged resiliently in a radial direction towards the axis of the syringe support 36, towards a position for co-operating with a complementary axial groove 64 forming anti-rotation means that are carried by the fastener endpiece 22. Naturally, the angular distribution of the pawls 76 on the inside surface 78 of the end 36D is selected in such a manner that the pawls 76 can co-operate with the complementary axial grooves 64 carried in the fastener endpiece 22.

It should be observed that it is possible to adapt the shape, the number, and the arrangement of the various pawls described above so as to adapt them to the fastener endpiece with which they are to co-operate. One advantage is to be able to adapt the device to different types of syringe and endpiece.

In another variant, as shown in FIG. 9, the safety device may have third complementary anti-rotation means 86 for constraining the support 36 in rotation relative to the sheath 34 about their respective axes. More precisely, these third means 86 are activated at least during the axial displacement of the sheath 34 and the support 36 relative to each other from the position in which the syringe needle 28 is uncovered towards the position in which said needle 28 is retracted.

For example, these third complementary means 86 comprise at least one axial spline 88 generally in the form of a flat carried by the support 36, extending axially in an upper portion of the support 36, including the proximal end 36P. This spline 88 is designed to co-operate with an axial notch (not shown) of generally complementary shape formed in an inner side wall of the annular groove 86 of the housing for the spring 42. Preferably, the third means 86 comprise two diametrically-opposite splines and two complementary notches. Because of the presence of these third means 86, when starting to relax the spring 42, any unwanted rotation thereof can be avoided.

It should be observed that the third means 86 may take the form, as in the other variant described above, of an axial spline 88 carried by the support 36, or as in FIG. 2, of a groove 54 formed in the support 36. With an axial spline 88, it should be observed that guidance is particularly robust and there is no risk of the spline 88 disengaging from the notch in the groove 84 during axial movement of the support 36 relative to the sheath 34 from which the position in which the syringe needle 28 is uncovered to the position in which the needle 28 is retracted.

Preferably, the assembly 10 is provided to the user in a configuration such that the pawls 66 and 76 are engaged in the complementary grooves 64. Where necessary, provision can be made during assembly of the syringe 12 in the safety device 23 for a small turning operation of the fastener endpiece 22, preferably by actuating the plug 24 in its direction for screw-tightening into the endpiece 22, so as to ensure that the pawls 66 snap into the corresponding grooves 64. Nevertheless, if the pawls 66 are not engaged in the grooves 64 when the assembly 10 is used, a user seeking to unscrew the plug 24 in order to replace it with the needle carrier 26 will cause the fastener endpiece 22 to turn sufficiently to bring the pawls 66 into coincidence with the grooves 64. There is therefore no need for the user of the assembly 10 to perform any special actions, other than unscrewing the plug 24 as is required in any event for it to be replaced by the needle carrier 26, with that sufficing to prevent the fastener endpiece 22 from turning relative to the sheath 34.

The invention is not limited to the embodiment described above.

In particular, the generally crenellated shape of the outline of the endpiece 22 may be defined by a variety of shapes other than axial grooves, for example grooves with non-parallel edges, sloping bottoms, ends that are open or closed, etc.

The pawls may be of a variety of shapes complementary to the crenellated outline of the endpiece 22.

It will be understood that the variants described above can optionally be combined with all of the functions described above.

What is claimed is:

1. A safety device for a liquid injection syringe having a syringe needle, the safety device comprising:
   a syringe body of generally tubular shape and forming a reservoir for liquid;
   a fastener endpiece of generally annular shape, the fastener endpiece being configured to allow a needle carrier to be screwed thereon so as to fasten the needle carrier on the syringe body and being fitted onto the syringe body;
   a protective sheath of generally tubular shape; and
   a syringe support of generally tubular shape and being received inside the sheath such that the syringe support is substantially coaxial with the sheath, wherein:
      the sheath and the syringe support are movable axially relative to each other between two positions, an uncovered position of the syringe needle, and a covered position of the syringe needle where the syringe needle is covered after an injection into a patient, the sheath at least partly covering the syringe needle when in the covered position,
      the syringe support includes a first anti-rotation means for constraining rotation of the syringe support about its axis, the first anti-rotation means including at least one pawl urged resiliently into a position in which the at least one pawl is designed to co-operate with a corresponding axial groove located on the annular fastener endpiece, and
      the protective sheath and the syringe support include a second anti-rotation means for constraining the protective sheath and the syringe support in rotation relative to each other about their axes, the second anti-rotation means being activated when the sheath and the syringe support are in their relative uncovered position of the syringe needle.

2. The safety device according to claim 1, wherein the syringe support includes at least two diametrically-opposite anti-rotation pawls.

3. The safety device according to claim 1, wherein the at least one pawl is formed by an axial tab molded integrally with the syringe support and urged resiliently radially towards the axis of the syringe support, the at least one pawl being designed to co-operate with the corresponding axial groove formed in an outer peripheral surface of the fastener endpiece.

4. The safety device according to claim 3, wherein
   the sheath includes at least one radial setback; and
   when the sheath and the syringe support are in their relative uncovered positions of the syringe needle, the at least one radial setback is positioned to be radially aligned with the axial tab so as to allow the axial tab to move radially against a return force of the axial tab.

5. The safety device according to claim 4, wherein the axial tab is disposed on a distal end of the syringe support, and the radial setback is formed by an axial slot provided in a distal end of the sheath.

6. The safety device according to claim 1, wherein the second anti-rotation means includes at least one complementary pair constituted by a projection and a groove provided on at least one of the syringe support and the protective sheath.

7. The safety device according to claim 6, wherein the projection of the second anti-rotation means is provided on a proximal end of the syringe support, and the groove of the second anti-rotation means is formed by a slot provided in a proximal end of the protective sheath.

8. The safety device according to claim 6, wherein the second anti-rotation means includes two diametrically-opposite complementary pairs, each of the complementary pairs comprising a projection and a groove.

9. The safety device according to claim 1, further including a third anti-rotation means for constraining the syringe support and the sheath in rotation relative to each other about their axes, the third anti-rotation means being activated during axial displacement of the sheath and the syringe support relative to each other from the uncovered position of the syringe needle towards the covered position of the syringe needle.

10. The device according to claim 1, wherein the at least one pawl does not restrict an axial movement of the fastener endpiece relative to the syringe support.

11. The device according to claim 1, wherein the corresponding axial groove on the fastener endpiece extends along an entire length of the fastener endpiece.

12. The device according to claim 1, wherein the first anti-rotation means and the second anti-rotation means prevent rotation of the sheath and the syringe body relative to the fastener endpiece when the needle carrier is fastened to or removed from the fastener endpiece.

13. A syringe assembly comprising:
   a liquid injection syringe including a syringe body of generally tubular shape forming a reservoir for liquid;
   a fastener endpiece of generally annular shape, the fastener endpiece being configured to allow a needle carrier to be screwed thereon so as to fasten the needle carrier to the syringe body and being fitted on the syringe body; and
   a safety device for the liquid injection syringe, the safety device including:
      a protective sheath of generally tubular shape; and
      a syringe support of generally tubular shape and being received inside the sheath such that the syringe support is substantially coaxial with the sheath, wherein:
         the sheath and the syringe support are movable axially relative to each other between two positions, an uncovered position of the syringe needle, and a covered position of the syringe needle where the syringe needle is covered after an injection into a patient, the sheath at least partly covering the syringe needle when in the covered position,
         the syringe support includes a first anti-rotation means for constraining rotation of the syringe support about its axis, the first anti-rotation means including at least one pawl urged resiliently into a position in which the at least one pawl is designed to co-operate with a corresponding axial groove located on the annular fastener endpiece, and
         the protective sheath and the syringe support include a second anti-rotation means for constraining the protective sheath and the syringe support in rotation relative to each other about their axes, the second anti-rotation means being activated when the sheath and the syringe support are in their relative uncovered position of the syringe needle.

14. The syringe assembly according to claim 13, wherein the fastener endpiece is designed to co-operate with a plug by a screw-fastening for closing the liquid injection syringe or the needle carrier.

15. A syringe assembly comprising:
   a liquid injection syringe including a syringe body of generally tubular shape forming a reservoir for liquid;
   a fastener endpiece of generally annular shape, the fastener endpiece being configured to allow a needle carrier to be screwed thereon so as to fasten the needle carrier to the syringe body and being fitted on the syringe body; and
   a safety device for the liquid injection syringe, the safety device including:
      a protective sheath of generally tubular shape; and
      a syringe support of generally tubular shape and being received inside the sheath such that the syringe support is substantially coaxial with the sheath, wherein:
         the sheath and the syringe support are movable axially relative to each other between two positions, an uncovered position of the syringe needle, and a covered position of the syringe needle where the syringe needle is covered after thew injection into a patient, the sheath at least partly covering the syringe needle when in the covered position,
         the syringe support includes a first anti-rotation means for constraining rotation of the syringe support about its axis, the first anti-rotation means including at least one pawl urged resiliently into a position in which the at least one pawl is designed to co-operate with a corresponding axial groove located on the annular fastener endpiece,
         the protective sheath and the syringe support include a second anti-rotation means for constraining the protective sheath and the syringe support in rotation relative to each other about their axes, the second anti-rotation means being activated when the sheath and the syringe support are in their relative uncovered position of the syringe needle, and
         an outer peripheral surface of the fastener endpiece is of generally crenellated shape defining a plurality of corresponding axial grooves that are angularly distributed.

* * * * *